(12) United States Patent
Hart et al.

(10) Patent No.: US 9,393,042 B2
(45) Date of Patent: Jul. 19, 2016

(54) COAXIAL TROCAR SEALS HAVNG SEQUENTIAL ADJACENT OPENINGS

(75) Inventors: Charles C. Hart, Rancho Santa Margarita, CA (US); John R. Brustad, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1014 days.

(21) Appl. No.: 13/483,457

(22) Filed: May 30, 2012

(65) Prior Publication Data

US 2012/0310165 A1 Dec. 6, 2012

Related U.S. Application Data

(60) Provisional application No. 61/492,041, filed on Jun. 1, 2011.

(51) Int. Cl.
*A61B 17/34* (2006.01)
*A61M 39/06* (2006.01)
*A61B 17/02* (2006.01)

(52) U.S. Cl.
CPC ......... *A61B 17/3462* (2013.01); *A61B 17/0218* (2013.01); *A61M 39/06* (2013.01); *A61M 2039/062* (2013.01); *A61M 2039/064* (2013.01); *A61M 2039/0633* (2013.01); *A61M 2039/0686* (2013.01)

(58) Field of Classification Search
CPC .............. A61M 39/045; A61M 39/06; A61M 39/0606; A61M 2039/064; A61M 2039/2426; A61M 2039/24; A61M 2039/0633; A61M 2039/062; A61M 2039/0686; A61B 17/3462; A61B 17/3423; A61B 17/3498
USPC ............. 604/164.01, 167.01, 167.02, 167.03, 604/167.04, 167.06
See application file for complete search history.

(56) References Cited

U.S. PATENT DOCUMENTS

| | | | |
|---|---|---|---|
| 5,000,745 A | 3/1991 | Guest et al. | |
| 5,176,652 A * | 1/1993 | Littrell | A61M 39/0606 137/849 |
| 5,342,315 A * | 8/1994 | Rowe | A61B 17/3462 604/167.06 |
| 5,385,552 A * | 1/1995 | Haber | A61B 17/34 604/167.03 |
| 5,389,081 A * | 2/1995 | Castro | A61B 17/3462 251/212 |
| 5,743,884 A | 4/1998 | Hasson et al. | |
| 6,086,570 A * | 7/2000 | Aboul-Hosn | A61M 39/0606 251/149 |
| 6,610,031 B1* | 8/2003 | Chin | A61M 39/045 604/167.04 |
| 6,981,966 B2 | 1/2006 | Green et al. | |
| 7,081,106 B1 | 7/2006 | Guo et al. | |
| 2003/0195472 A1* | 10/2003 | Green | A61B 17/34 604/167.04 |
| 2004/0230161 A1 | 11/2004 | Zeiner | |
| 2005/0131349 A1* | 6/2005 | Albrecht | A61B 17/34 604/167.06 |
| 2008/0249475 A1* | 10/2008 | Albrecht | A61B 17/3498 604/167.06 |
| 2009/0093682 A1* | 4/2009 | Izzo | A61B 17/3462 600/201 |
| 2010/0057009 A1* | 3/2010 | McQueen | A61M 39/06 604/164.03 |
| 2010/0204655 A1* | 8/2010 | Melsheimer | A61M 39/06 604/167.03 |
| 2011/0087159 A1* | 4/2011 | Parihar | A61B 17/34 604/26 |

* cited by examiner

*Primary Examiner* — Bhisma Mehta
*Assistant Examiner* — Jenna Zhang
(74) *Attorney, Agent, or Firm* — Patrick Ikehara

(57) ABSTRACT

An instrument seal of a surgical access device is provided and includes a plurality of nested coaxial seals arranged to cooperate and form a complete, circumferential seal around an inserted instrument.

26 Claims, 13 Drawing Sheets

COAXIAL TROCAR SEALS HAVNG SEQUENTIAL ADJACENT OPENINGS

CROSS-REFERENCE TO RELATED APPLICATIONS

This application claims the benefit of U.S. Provisional Application No. 61/492,041, filed on Jun. 1, 2011, the entire disclosure of which is incorporated by reference as if set forth in full herein.

BACKGROUND

The present invention relates generally to seals and more particular to nested seals for use in surgical access ports, commonly referred to as trocars.

Instrument seals generally comprise a septum seal that is sized and configured to work within a specified range of instrument diameters, e.g., from 5 mm to 12 mm. This range requires that the orifice of the instrument seal stretch to accommodate the largest instruments. However, it must also seal around the outer diameter of the smallest instruments when they are inserted therethrough and while they are manipulated within a working channel that accommodates the largest instruments. The side-to-side or off-axis motion of the smaller instruments within the large working channel may create leakage as the orifice is deformed by the inserted instrument.

To deal with this challenge, instrument seals that float in response to the motion of an inserted instrument so that the orifice may be sized to the instruments accurately were developed. The floatation of the seal removes orifice deformation caused by the motion of an inserted instrument. Instead, the orifice is encouraged to follow the motion of the inserted instrument. However, there remains a need to continue to expand the useful range of instrument seals in surgical access devices even further. For instance, an instrument range between 3 mm and 16 mm is presently a developing requirement. This range may exceed the elastic properties of materials that are appropriate for such instrument seals.

SUMMARY

In various embodiments, an instrument seal for surgical access ports is provided that comprises a plurality of coaxial seals that cooperate to form a complete, circumferential seal around an inserted instrument. Each of the coaxial seals forms a partial seal upon the inserted instrument and is only required to stretch in one direction in response to the insertion of the instrument. Each of the adjacent, coaxial seals responds in similar fashion to complete the seal upon the inserted instrument. The orifice defined by the cooperative, coaxial seals is centrally located and comparatively small even though the openings of the seals are structurally off-center and substantially larger than the cooperative orifice.

In one embodiment, an instrument seal comprises a plurality of nested coaxial seals arranged to cooperate and form a complete, circumferential seal around an inserted instrument, each of the plurality of coaxial seals forming a partial seal upon the inserted instrument and stretching in one direction in response to the inserted instrument; and each of the plurality of coaxial seals has a cylindrical center portion and a distal tapered portion with an opening disposed in a portion of the distal tapered portion.

In one embodiment, an instrument seal comprises a plurality of nested coaxial seals arranged to cooperate and form a complete, circumferential seal around an inserted instrument and each of the plurality of coaxial seals forms a partial seal upon the inserted instrument and stretching in one direction in response to the inserted instrument. Also, each of the plurality of coaxial seals are elongate having a length greater than a width of the seal and each of the plurality of coaxial seals have a proximal opening and a distal opening. The proximal opening of each of the plurality of coaxial seals has a center aligned with a longitudinal axis of the instrument seal and the distal opening of each of the plurality of coaxial seals has a center not aligned with the longitudinal axis of the instrument seal.

Many of the attendant features of this invention will be more readily appreciated as the same becomes better understood by reference to the following detailed description and considered in connection with the accompanying drawings in which like reference symbols designate like parts throughout.

DETAILED DESCRIPTION

Figure 1:
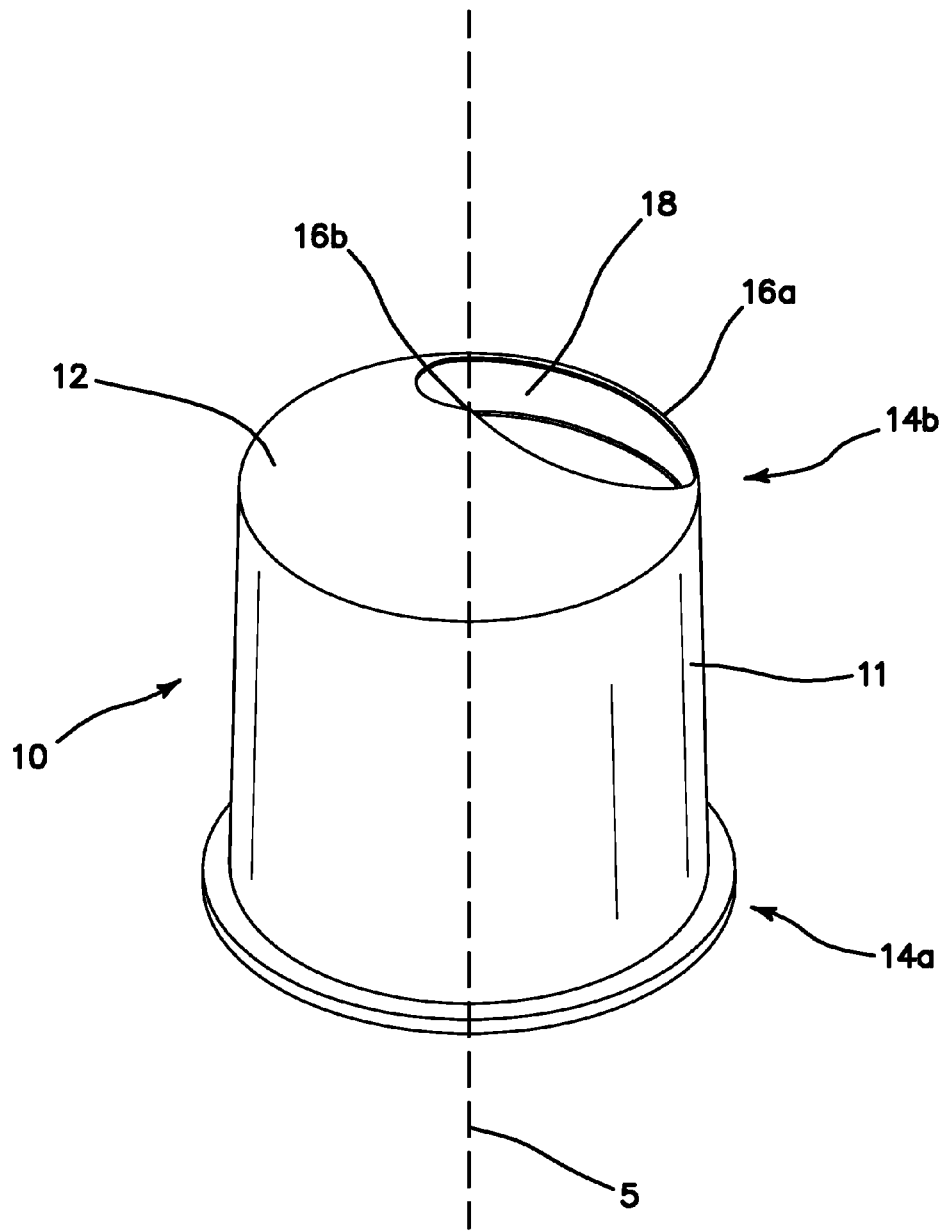
FIG. 1 is a perspective end view of a coaxial seal in accordance with various embodiments of the present invention.

A trocar seal is provided that includes a plurality of concentric, coaxial or layered seals with off-center distal openings relative to the longitudinal axis of the trocar seal. The seals and their openings cooperatively delimit or define an operative orifice through the seals when an instrument is inserted therethrough. The seals seal against the outer diameter of the inserted instrument and in one embodiment forms a zero seal when no instrument is inserted through the seals.

In one embodiment, a separate additional zero closure valve such as a duckbill seal and/or a separate additional instrument seal such as a septum seal is included with the trocar seal. In accordance with various embodiments, a trocar seal comprises a conical, frustaconical or cylindrical seal comprising a plurality of concentric seals, each having a distal end opening that is off-center to the axis of the seal assembly. In one embodiment, each distal end opening is sized to be the maximum instrument diameter size that the trocar seal can accommodate.

As illustrated in FIGS. 1-4D, in one embodiment, the trocar seal comprises at least four seals 10, 20, 30 and 40. A first seal 10 comprises an elongate cylindrical center portion 11 with a distal tapered or conical portion 12. The proximal end 14a of the first seal is open and is sized and configured to accommodate a working channel of the surgical access device or trocar. The proximal end in one embodiment includes a flange or an extended peripheral portion 49 utilized for example to secure the trocar seal to a seal housing (not shown). The distal end 14b is substantially closed except for an opening or aperture 18 that extends from approximately the center or center point 16b of distal conical portion 12 to the outer edge 16a of the seal. The opening in one embodiment has a radius or width that is equal to the radius of the trocar seal. However, the opening extends only from the center 16b of the trocar seal to the outer edge 16a and can appear to be a semi-circle as viewed from the bottom of the trocar seal. The opening 18 does not extend past the center point 16b of the distal tapered portion 12 and/or is not circular.

A second seal 20 comprises an elongate cylindrical center portion 21 with a distal conical or tapered portion 22. The proximal end is open and is sized and configured to provide or be aligned with a working channel of the surgical access device or trocar. The distal end is substantially closed except for an opening or aperture 28 that extends from approximately the center of the working channel to the outer edge of the seal member. The opening in one embodiment has a radius or width that is equal to or substantially corresponds to the radius of the trocar seal. However, the opening extends only from the center 26b of the trocar seal to the peripheral or outer edge 26a. The opening in one embodiment appears to be a semi-circle or portions thereof as viewed from the bottom of the trocar seal. The second seal 20 is installed over the first seal 10 concentrically and clocked or rotated axially to a second offset position. In one embodiment, the second offset seal position is about 90 degrees from the position of the first seal 10, i.e., the first offset position, such that the distal openings of the first and second seals are not aligned and/or rotationally offset from each other. The center of the first and second seals remains aligned to each other and the axis 5 of the trocar seal. Also, the opening 28 does not extend past the center point 26b of the distal tapered portion 22 and/or is not circular.

A third seal 30 comprises an elongate cylindrical portion 31 with a distal conical portion 32. The proximal end and distal end of the third seal are similar to the first and second seals. The opening 38 in the distal end of the third seal is also similar to the other seals extending from approximately the center 36b of the seal to the outer edge 36a of the seal. The third seal 30 is installed over the first and second seals 10, 20 concentrically and clocked or rotated axially to a third offset position.

In one embodiment, the third offset seal position is about 90 degrees from the second offset position of the second seal 20 such that the distal openings of the second and third seals 20,30 are not aligned or are rotationally offset from each other. The center of the first, second and third seals 10,20,30 remain aligned to each other and the axis of the trocar seal. In one embodiment, the third offset seal position is about 180 degrees from the position of the first seal 10 such that the distal openings of the first, second and third seals 10,20,30 are not aligned or are rotationally offset from each other.

A fourth seal 40 like the first, second and third seal comprises an elongate cylindrical portion 41 with a distal conical portion 42. The proximal end, distal end and opening extending from approximately the center 46b of the seal to the outer edge 46a are also similar to the proximal ends, distal ends and openings of the other seals. The fourth seal 40 is installed over the first, second and third seals 10, 20, 30 concentrically and is clocked axially to a fourth offset position.

In one embodiment, the fourth offset seal position is about 90 degrees from the first and third offset position of the first and third seals 10,30 such that the distal openings of the first, second, third and fourth seals 10, 20, 30 and 40 are not aligned or rotationally offset from each other. The center of the first, second, third and fourth seals remain aligned to each other and the axis 5 of the trocar seal. In one embodiment, the fourth offset seal position is about 180 degrees from the second offset position of the second seal 20. In one embodiment, the openings of the first, second, third and fourth seals have diameters in which the majority of the size of the openings and/or diameters are offset or not aligned with the axis 5 of the trocar seal with the minority or a fraction of the size or diameters of the openings of each of the seals being aligned with the axis of the trocar seal.

Figure 2:
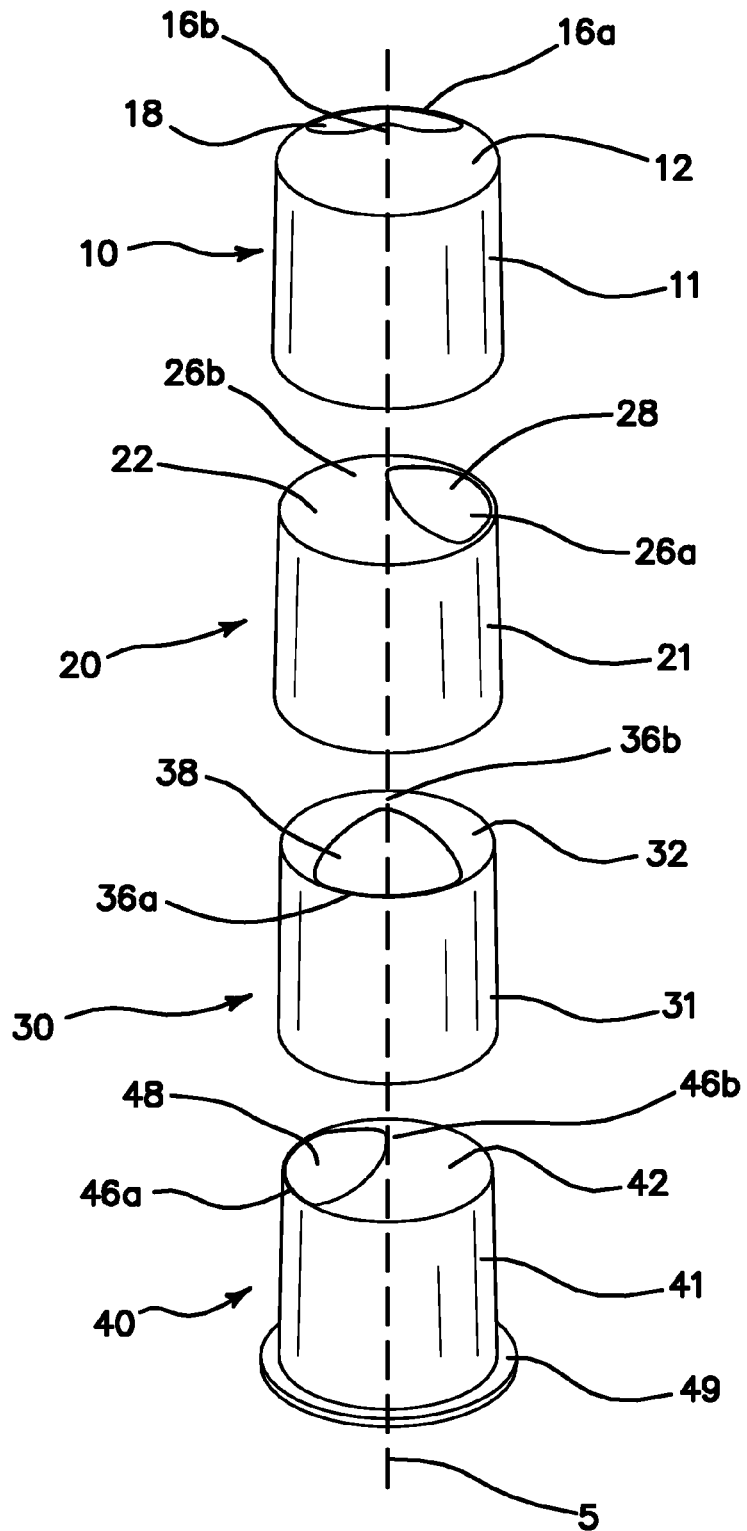
FIG. 2 is an exploded perspective view of a coaxial seal in accordance with various embodiments of the present invention.

In the illustrated embodiment of FIG. 2, the proximal end of the fourth seal 40 is the only seal that includes a flange or an extended peripheral portion 49 utilized for example to secure the trocar seal to the seal housing and the other seals 10, 20 and 30 are smooth without flanges. Additionally, in various embodiments, the proximal end of each seal has a radius or diameter smaller than the radius or diameter of the next seal. For example, the diameter of the proximal end of the first seal is smaller than the diameter of the second, third and fourth seals and the diameter of proximal end of the second seal is smaller than the diameter of the third and fourth seals with the proximal end of the fourth seal having the largest diameter. Similarly, the distal end of each seal in various embodiments has a radius or diameter smaller than the radius or diameter of the next seal with for example the distal end of the first seal having the smallest diameter and the distal end of the fourth seal having the largest diameter.

In one embodiment, the combination of the first, second, third and fourth seals 10, 20, 30 and 40 are positioned coaxially or nested together and form a complete occlusion of the working channel of the trocar seal as the distal openings of the seals meet at the center of the working channel. In another embodiment, the combination of seals is positioned coaxially or nested together and forms a partial occlusion of the working channel of the trocar seal. In one embodiment, a separate or additional zero closure valve may be included in either embodiment to provide or assist in the complete occlusion of the working channel when no instrument is within the working channel. For example, a zero seal is provided and the coaxial seals are nested within the zero seal. The zero seal in one embodiment is a duckbill made of a material being the same as the plurality of coaxial seals and/or the zero seal has a proximal flange. In various embodiments, a seal housing is provided with the coaxial seals disposed within the seal housing and a cannula removably coupled to the seal housing.

In various embodiments, the first, second, third and fourth seals 10, 20, 30 and 40 have a length greater than a width of the seal and the first, second, third and fourth seals have a proximal opening with a center aligned with the longitudinal axis 5 of the seal and a distal opening with a center not aligned with the longitudinal axis of the seal. Also, the seals are coaxial and each of the seals has an opening with a center not aligned with the longitudinal axis. The openings of each of the seals cooperatively define an orifice with a center aligned with the longitudinal axis with the openings of each of the seals being larger than the orifice defined by the seals. The opening of each of the seals starts from a perimeter of the cylindrical center portion intersecting the distal tapered portion and extends towards and not past a center point of the distal tapered portion of each seal. A center point of the distal tapered portion of each of the seals does not include an opening or portions thereof and in one embodiment the distal opening of each of the plurality of coaxial seals occupies a quarter portion of a surface area of a distal most portion of each of the plurality of coaxial seals. In various embodiments, the distal opening of each of the plurality of coaxial seals is triangular, elliptical or non-circular. Each of the seals forms a partial seal upon the inserted instrument and stretches in one direction in response to the inserted instrument.

Referring also now to FIGS. 5-12, a surgical access device or port in one embodiment comprises a seal housing 100, seals 10-40 and a cannula 110. The seal housing 100 is sized and configured to contain the seals and/or a zero closure valve 50 in a gas-tight relationship between the distal portion and the proximal portion of the seal housing 100. In one embodiment, the cannula 110 is elongate and tubular with portions textured and/or tapered that is connectable to the distal portion of the seal housing 100. The proximal portion of the seal housing 100 includes a cap securing the seal 10-40 and/or the zero closure valve 50 within the seal housing 100. One or more of the seals in one embodiment is configured within the seal housing allowing the seal to float or pendulate via flexible attachments, such as bellows, or other suitable arrangements. The proximal end of the seal 20 in one embodiment includes a flange or an extended peripheral portion 29 utilized for example to secure the trocar seal to the seal housing and the other seals 10, 30 and 40 are smooth without flanges. The proximal end of the zero closure valve 50 in one embodiment includes a flange or an extended peripheral portion 59 utilized for example to secure the trocar seal to the seal housing and/or to one or more of the other seals.

The trocar seal, in one embodiment, is fixed within the seal housing. In other embodiments, the trocar seal has a proximal end, a distal end and a length and the proximal end of the trocar seal can fit within or may be otherwise coupled to a flexible attachment to the seal housing. Through the flexible attachment, the trocar seal pendulates or floats radially under the influence of a moving instrument within the working channel. The proximal end of the trocar seal is open and has an inside diameter that defines the working channel or lumen of the access port. The lumen in one embodiment extends the length of the trocar seal up to the distal portion. The distal portion of the trocar seal provides a plurality of individual seals arranged coaxially and further arranged such that the off-center openings of the individual seals are approximately 90 degrees offset to each other axially.

In various embodiments, the seals are nested together to form a monolithic structure and in one embodiment the seals are nested together with the assistance of attachment features such as adhesive. In other embodiments, one or more of the seals are attached to each other, the seal housing, intermediary structures, such as bellows, rings and spacers, and/or other seals, such as zero and septum seals, via an attachment feature such as adhesive and/or mechanical attachments such as flanges, detents and recesses. In various embodiments, one or more of the seals only have a conical portion or have a distal portion that is substantially planar or flat with or without the cylindrical portion. However, the conical or tapered portion assists in guiding the instrument to the operative orifice and the stretching or extension of the opening in the seal along the specified direction. In such embodiments in which one or more seals has a cylindrical, tubular or elongate center portion with a tapered distal portion, the center portion has a length greater than the width of the seal and/or the center and tapered portion thereby allowing the inserted instrument to be directed towards the center or operative orifice defined by the seals and to allow movement of the seals to adjust to the inserted instrument and provide the operative orifice. In various embodiments, the openings of one or more of the seals may be shaped in other forms, such as triangular or elliptical, to facilitate the stretching or extension of the opening towards the operative orifice and/or to seal against the inserted instrument. It should be appreciated that no one seal seals against or is suitable to seal against the entire outer diameter of the inserted instrument. Each opening of each seal seals or surrounds only a portion of the inserted instrument. Also, only a portion of each opening of each seal defines the operative orifice and the seal around the inserted instrument.

In one embodiment, the first coaxial seal is positioned at 12 o'clock, the second coaxial seal at 3 o'clock, the third coaxial seal at 6 o'clock and the fourth coaxial seal at 9 o'clock axially. In various embodiments, the trocar seal include additional coaxial seals that arranged at different offset positions that provide additional sealing characteristics. In one embodiment, a fifth coaxial seal at 12 o'clock may eliminate the need for a check-valve or zero closure valve. As such, the reinforcement provided by the fifth seal may hold the coaxial seals in tight occlusion such that there is no retrograde gas flow when the working channel is vacant.

It may be appreciated that a typical round opening, corresponding to the appropriate range of instrument sizes, stretches or dilates to accommodate the largest instruments. The perimeter dilation of the opening may be nearly 400% and the area of the opening may increase up to 18 times. This makes the selection of material for the seal difficult as most elastomeric materials cannot match this requirement and those that do, are not generally durable enough for trocar seals. In addition, when elastomeric materials are highly stretched, they exhibit the tendency to nick and tear and small defects in the seal will magnify under stress.

Conversely, the off-center openings of each of the seals is only required to stretch or dilate approximately 50 to 100% and in one direction only. The selection of material of the seals is thus less restrictive and in one embodiment can fit the specific needs of the device, e.g., a material such as a silicone elastomer may be used. In one embodiment, one or more of the seals could have a compounded lubricant that reduces friction between an instrument and the seal material. However, such materials are typically not sufficiently durable for use in a laparoscopic or surgical access device since they are sensitive to sharp or pointed instruments especially when stretched. The off-center openings of the seals however prevent the material from being over stressed to a degree that reveals this sensitivity or makes the material vulnerable to "notching" and tearing.

In one embodiment, one or more of the individual seals may be made of one or more different materials. For instance, the innermost or most proximal seal or portions thereof may be made from a very durable, reinforced material to resist snagging or tearing. The material used for the innermost seal in one embodiment may also exhibit the least amount of frictional drag upon the instrument. However, the seal made from such material may not exhibit the desired sealing properties by itself. The second seal may be made from a similar material. In one embodiment, the first and second instrument seals thus provide guidance for the instrument and protection for the adjacent seals. In another embodiment, the third and fourth coaxial seals may be made from very soft, compliant, occlusive material such as silicone, Krayton™, C-Flex™ or the like. The third and fourth seals and in one embodiment a fifth or sixth seal cooperate to form an occlusive seal upon the inserted instrument. In one embodiment, for example, the first and third seals are made of a puncture resistant material and the second and fourth seals are made of a compliant material but not puncture resistant material. Accordingly, the number, size and/or material of the seals can vary to accommodate different sealing, protection and/or friction properties and combinations thereof rather than relying on a single seal to provide all the desired properties or forgo specific properties in lieu of providing other properties.

In one embodiment, the number of the coaxial seals can include less than four seals, e.g., two or three, or greater than four seals. Additionally, the size or shapes of the openings can vary to facilitate sealing an inserted instrument and/or the valve when an instrument is not inserted therein. In one embodiment, the seals are spaced axially from each other. For example, the conical portions are spaced from each other via spacers or raised portions inserted or attached to the seals to create a predetermined distance between sequential or coaxial seals and thereby facilitate the stretching of the openings in one direction, e.g., towards the operative orifice. In one embodiment, the seals are impregnated with lubricant or similar material or coating to facilitate insertion or withdrawal of an instrument or a specific use, e.g., a scope cleaner. In various embodiments, the coaxial, nested seal members have a tapered distal end. The taper allows an instrument to glide toward the enlarged off-axis opening. Additional guidance and/or protection for the seals may be provided by a plurality of plastic shields 60.

Figure 3:
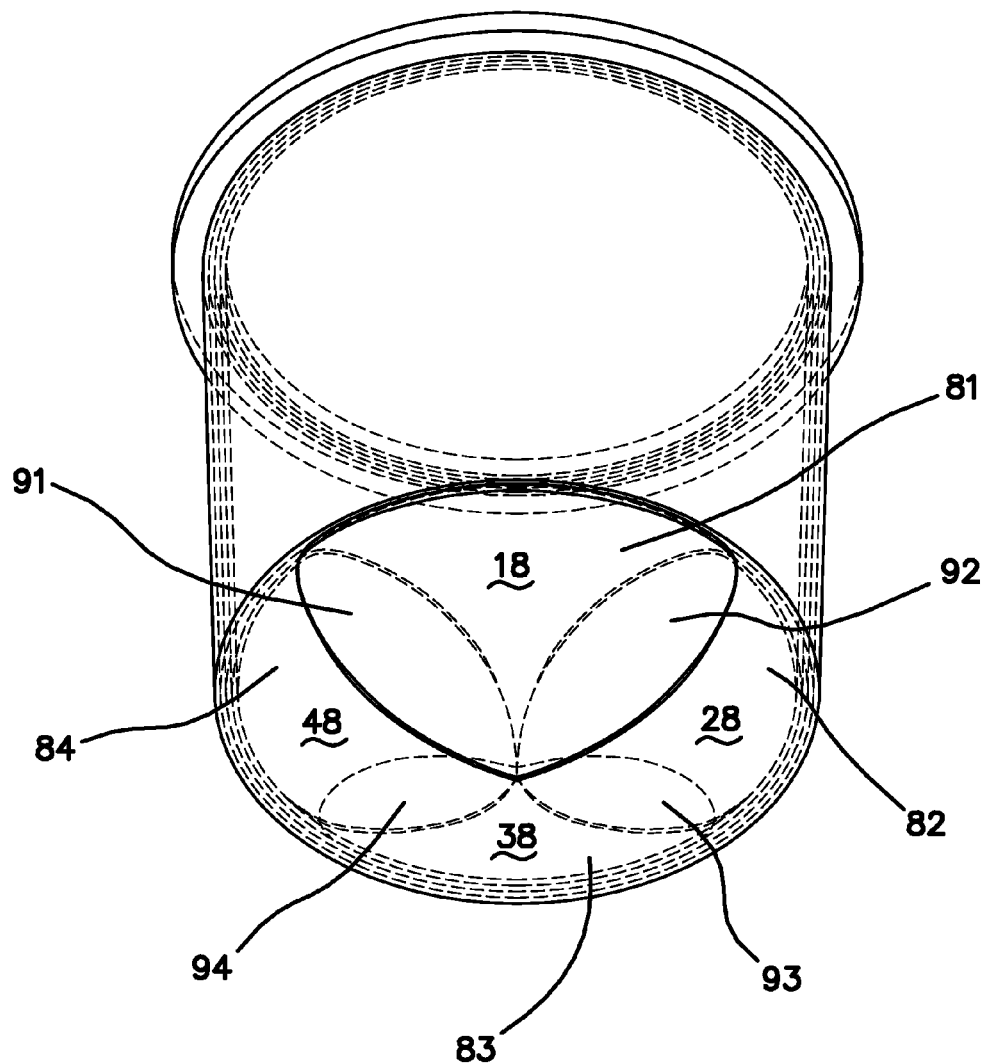
FIG. 3 is a perspective hidden-line view of a coaxial seal in accordance with various embodiments of the present invention.
Figure 4A:
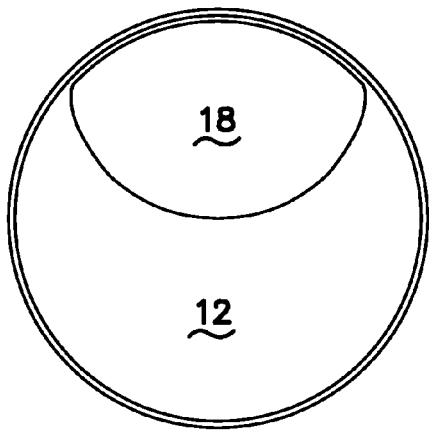
FIGS. 4A-D are distal end views of coaxial seals in accordance with various embodiments of the present invention.
Figure 4B:
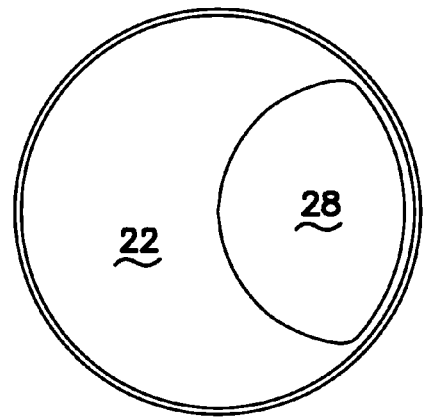
Figure 4C:
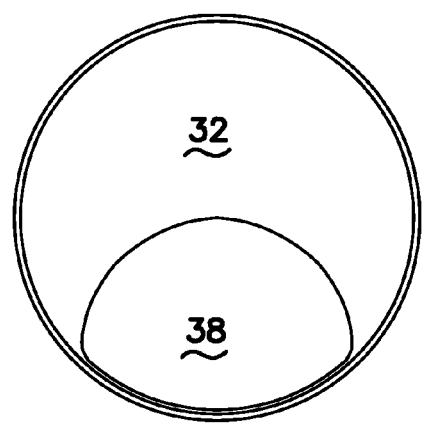
Figure 4D:
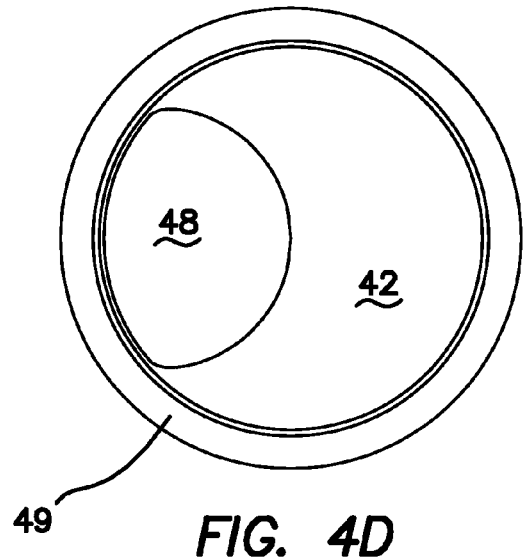
Figure 5A:
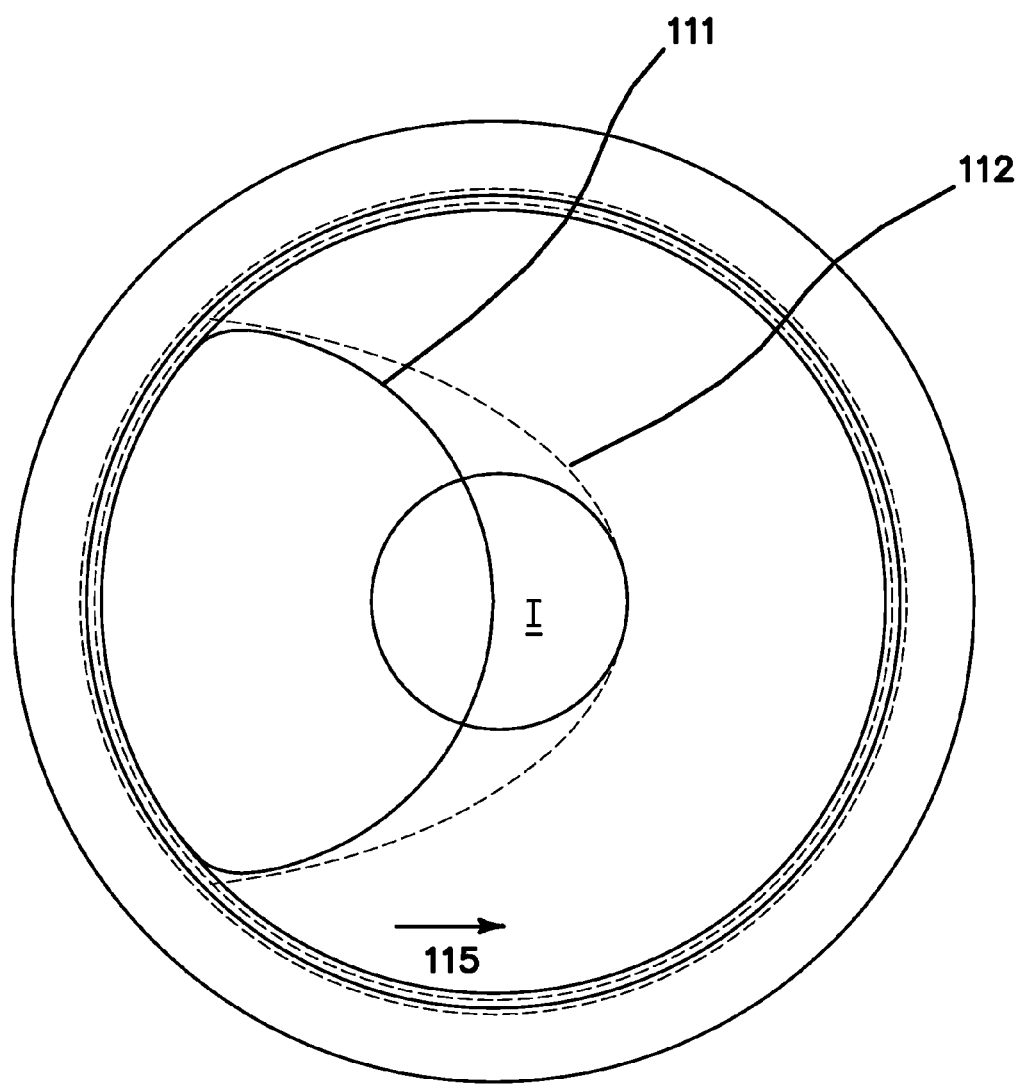
FIG. 5A is an enlarged distal view of the trocar seal with a small instrument in place with hidden lines showing the overlapping portions in accordance with various embodiments of the present invention.
Figure 5B:
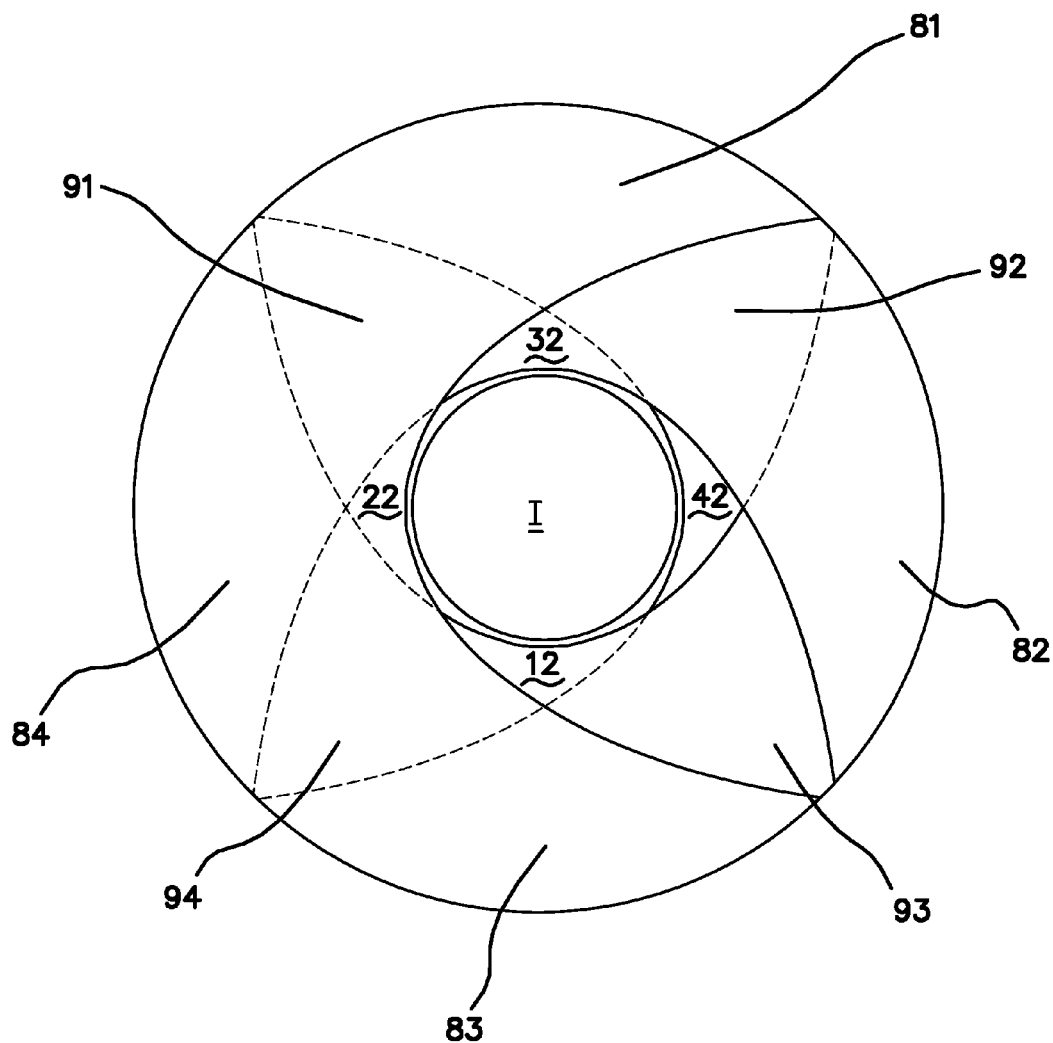
FIG. 5B is an enlarged proximal view of one of the seals with a small instrument in place with a hidden line showing the enlarged opening in accordance with various embodiments of the present invention.
Figure 6:
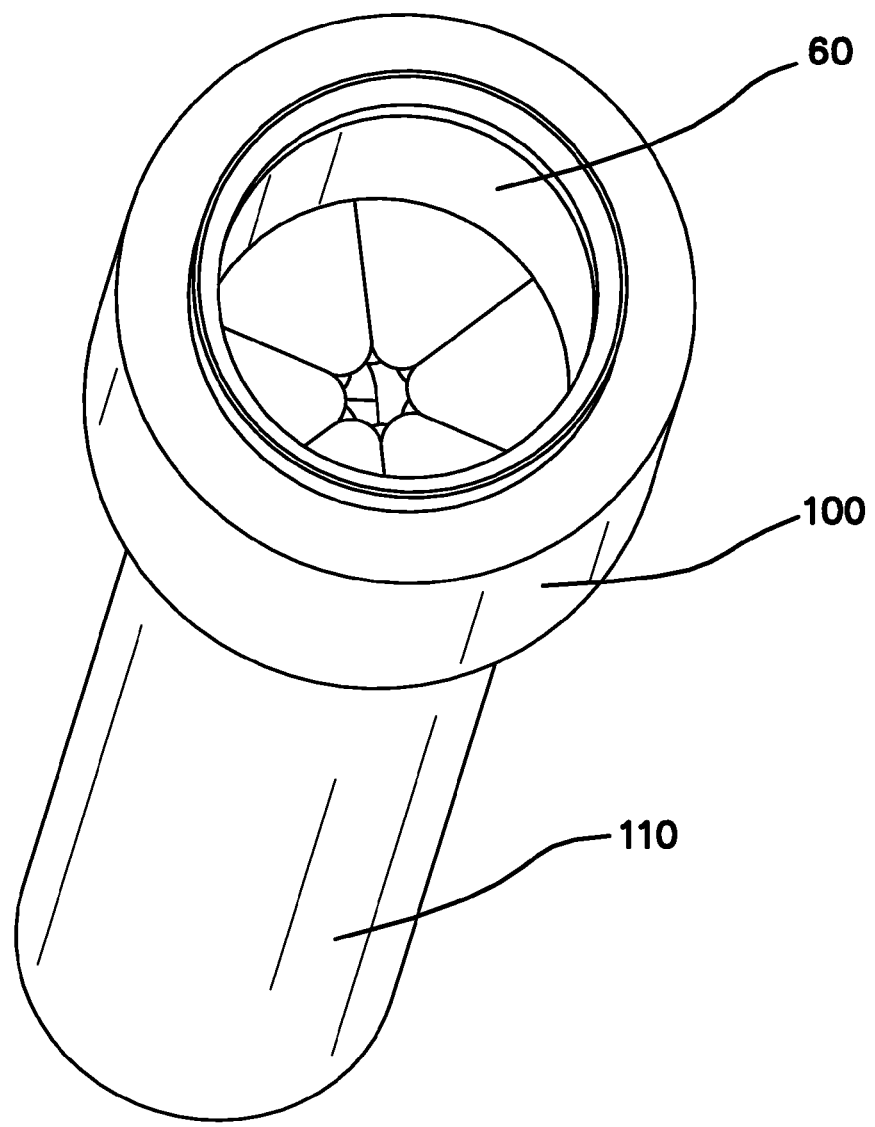
FIG. 6 is a perspective view of a surgical access port in accordance with various embodiments of the present invention.
Figure 7:
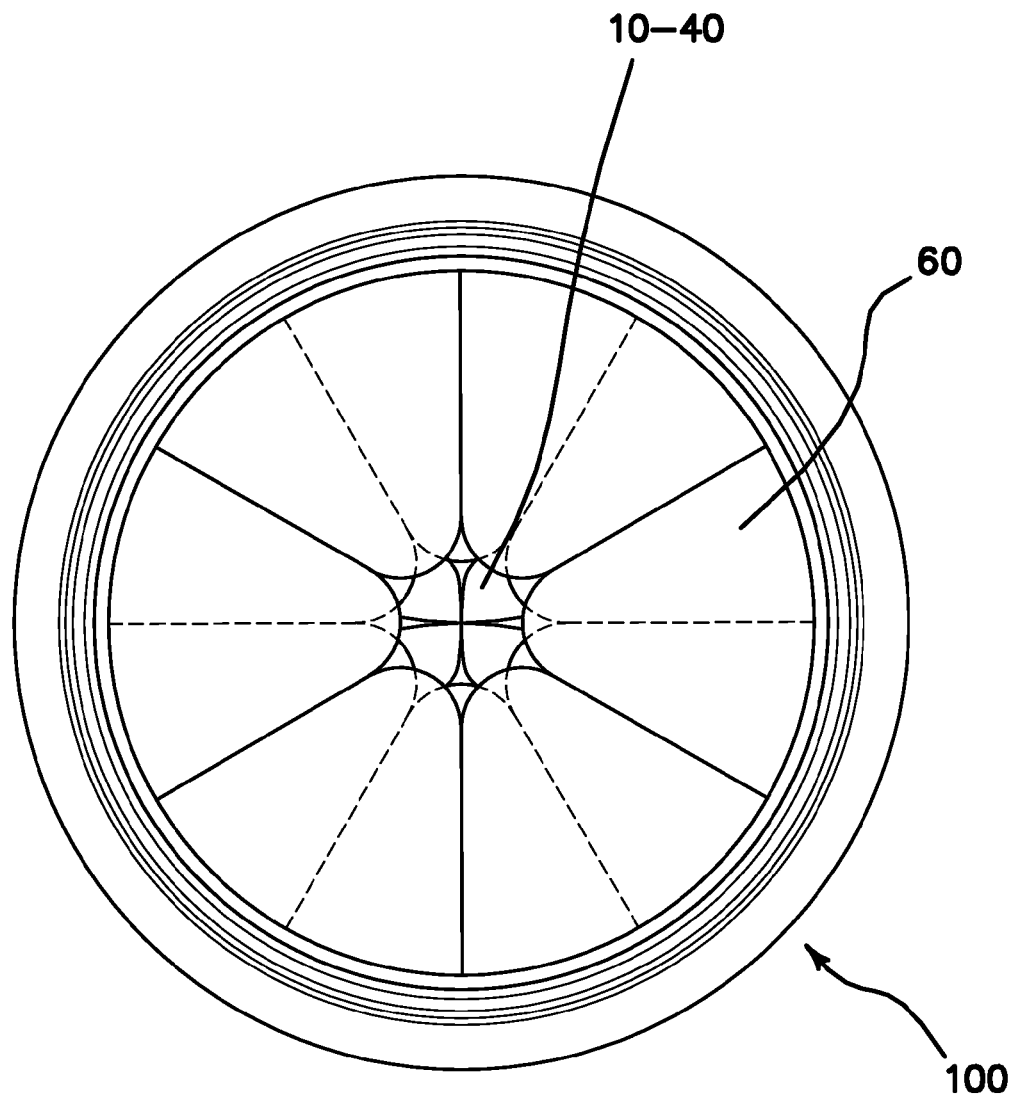
FIG. 7 is a proximal end view of a surgical access port in accordance with various embodiments of the present invention.
Figure 8:
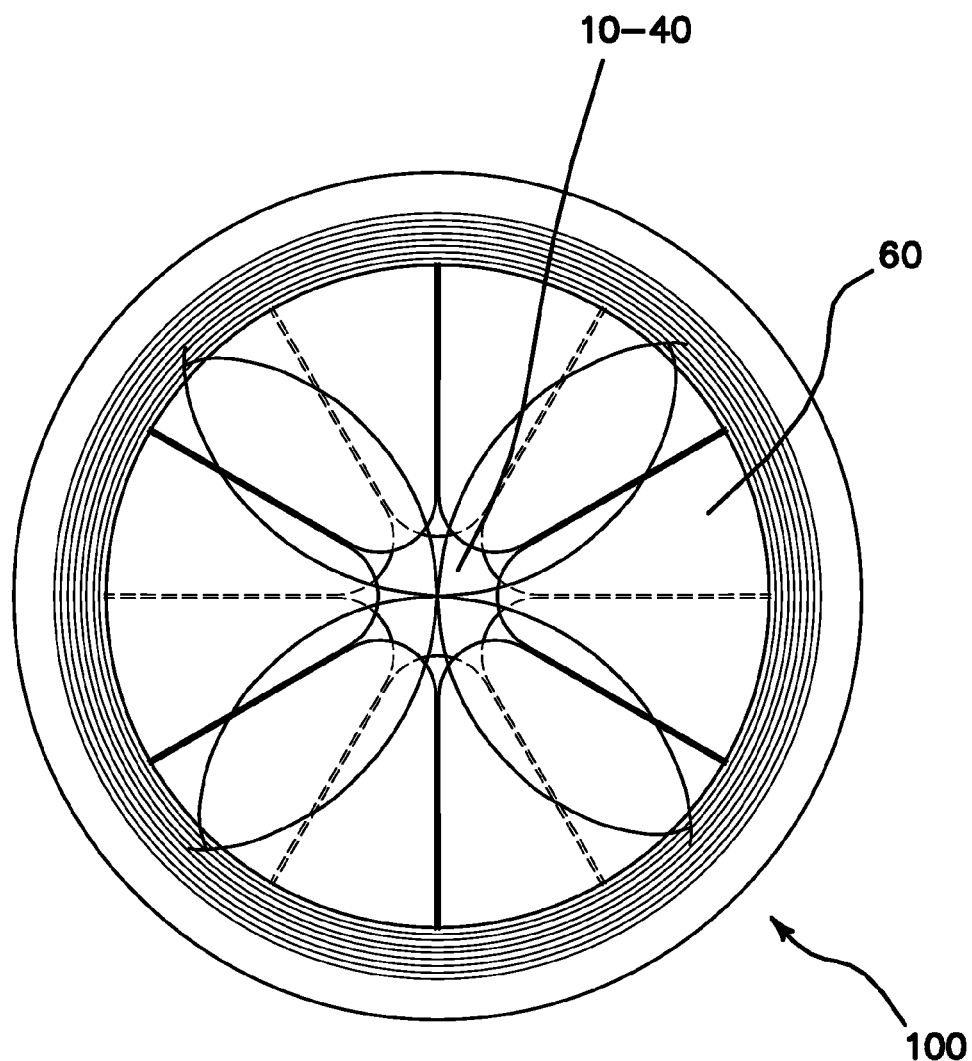
FIG. 8 is a proximal end view of a surgical access port with hidden lines showing overlapping portions in accordance with various embodiments of the present invention.
Figure 9:
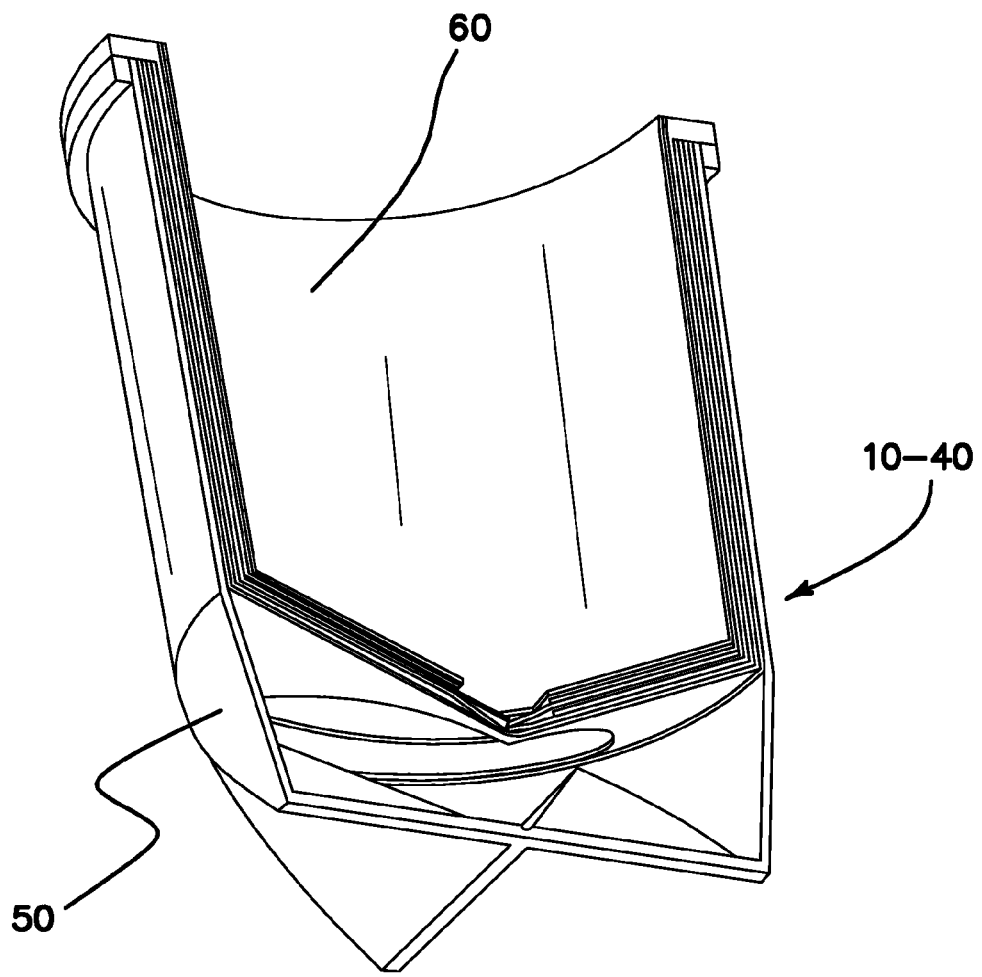
FIG. 9 is a perspective section view of a trocar seal in accordance with various embodiments of the present invention.
Figure 10:
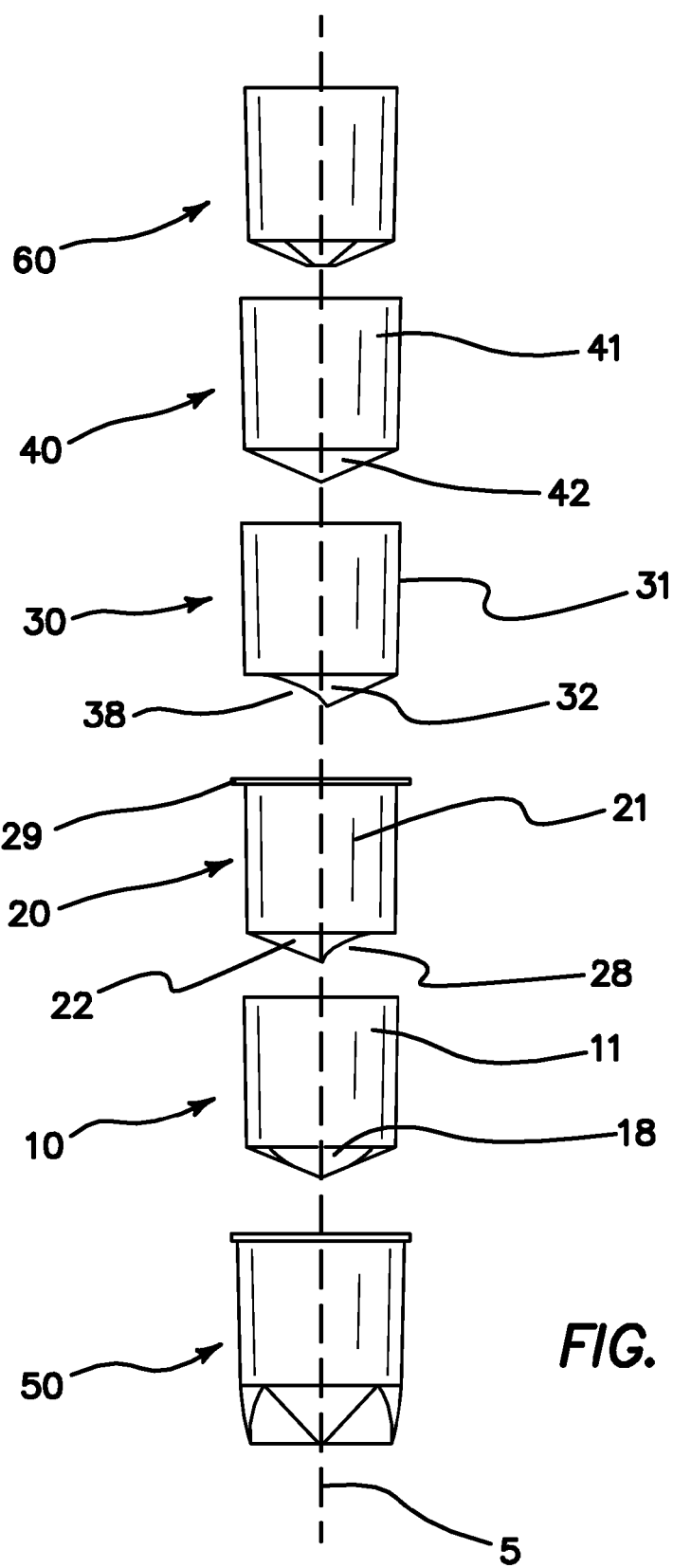
FIG. 10 is an exploded view of a trocar seal in accordance with various embodiments of the present invention.
Figure 11:
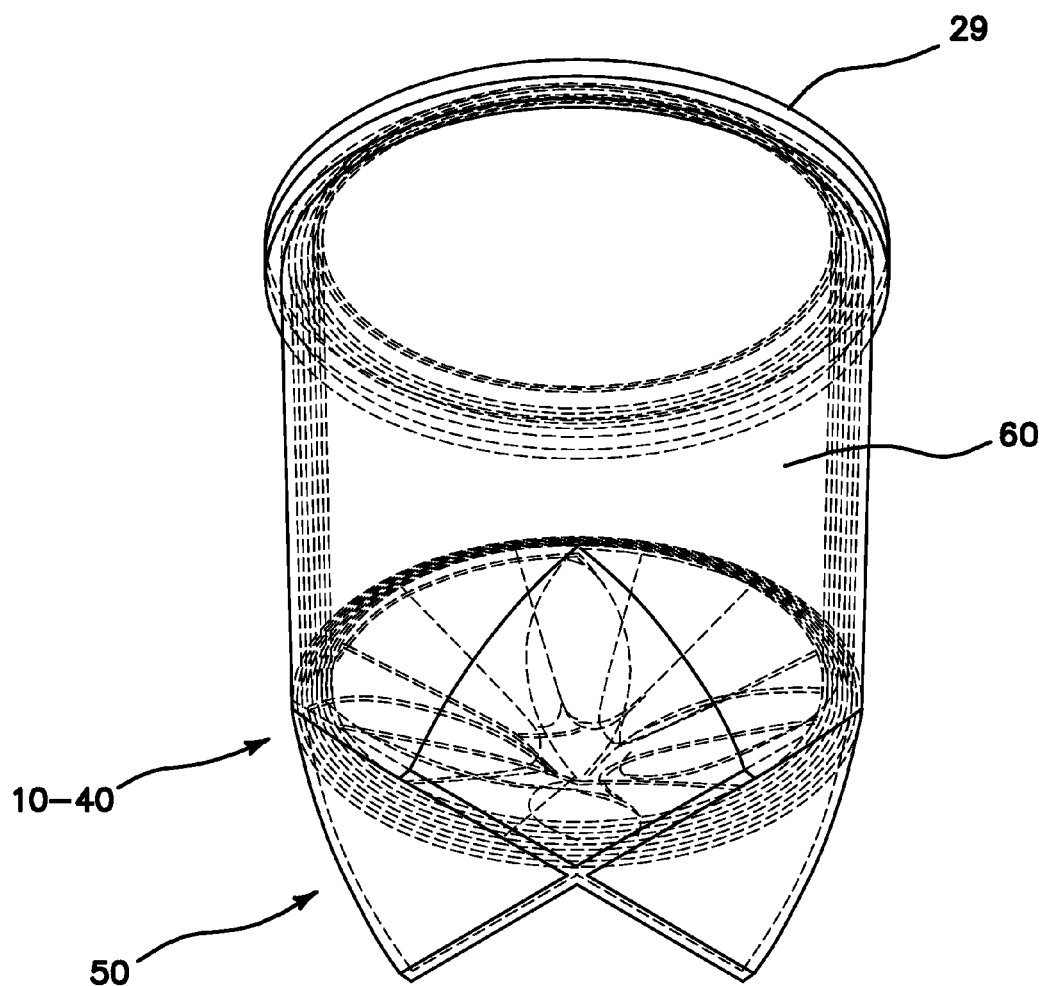
FIG. 11 is perspective view of a trocar seal with hidden lines showing various components of the trocar seal in accordance with various embodiments of the present invention.
Figure 12:
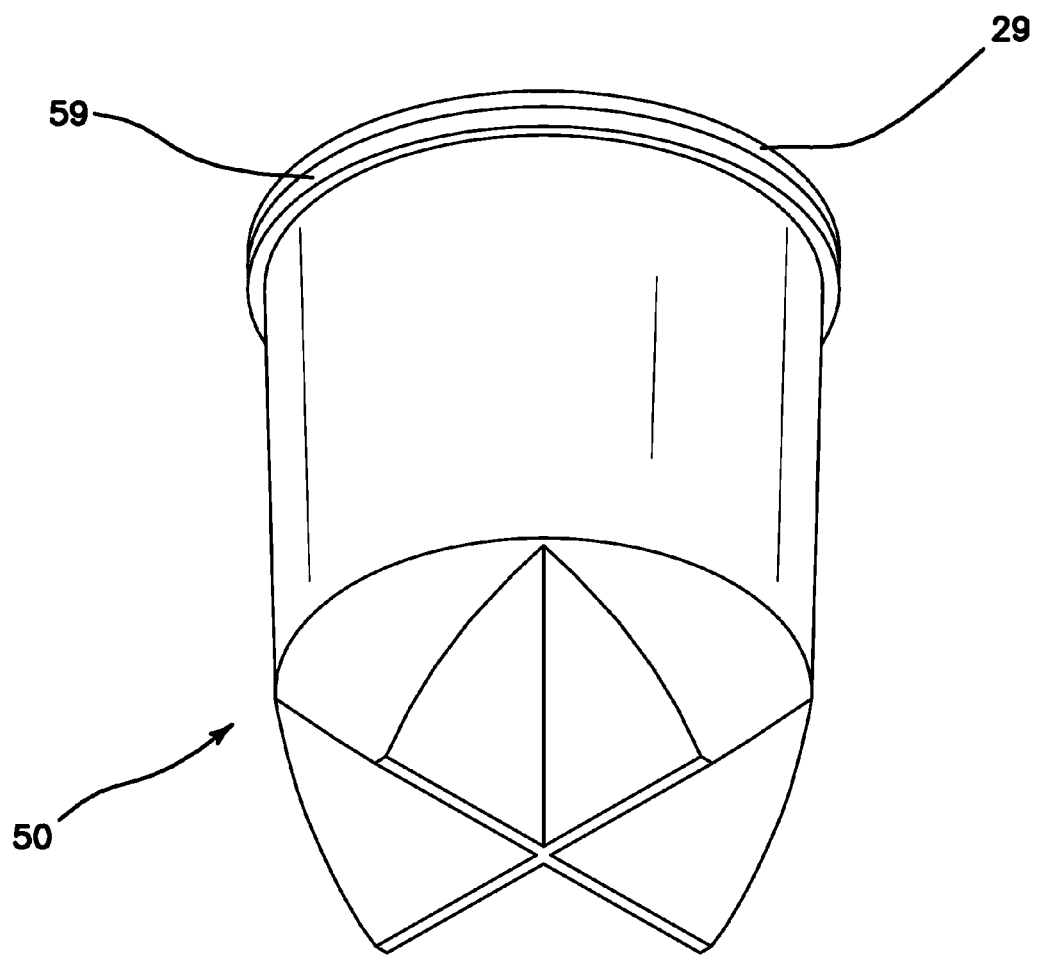
FIG. 12 is perspective view of a trocar seal in accordance with various embodiments of the present invention.

To exemplify the dilating of the seals 10-40 when an instrument I is inserted, nested or stacked portions of the seals are shown in FIGS. 3 and 5B in which stacked portion 81 includes portions of seals 10, 20 and 40; stacked portion 82 includes portions of seals 20, 30 and 40; stacked portion 83 includes portions of seals 10, 30 and 40; and stacked portion 84 includes portions of seals 10, 20 and 30. Additionally, stacked portion 91 includes portions of two seals, seals 10,20; stacked portion 92 includes portions of seals 20,40; stacked portion 93 includes portions of seals 30,40; and stacked portion 94 includes portions of seals 10,30. Additionally, to exemplify the dilating of a portion of an opening in an seal when an instrument I is inserted, an enlarged opening edge 112 is shown as a hidden line in FIG. 5A with stretching or extension of the opening only in a direction away from the center, i.e., in the direction shown by arrow 115, from the initial or relaxed state of the opening edge 111. Ramps or similar projections in various embodiments are included along a portion of one or more of the openings of the seals to enhance sealing/stretching of the seal and facilitate insertion or removal of the instruments. In other embodiments, one or more seals include curved or slanted regions away from the center of the seal to facilitate stretching or extension of the openings away from the center to accommodate an inserted instrument. In various embodiments, portions of one or more of the openings of the seals are rounded, curvilinear or similar shaped or dimensioned to facilitate sealing against a portion of an inserted instrument or stretching towards specific direction, e.g., away from the center of the trocar seal.

It can also be appreciated that the trocar seal as described in various embodiments do not require special material as in typical trocar seals that need to provide ample stretching to accommodate various instrument size ranges and radial motion of instruments used with the seals. Additionally, the use of typical adaptors that manually adjust the size of the aperture through which an instrument passes can also be avoided reducing operational and manufacturing difficulties.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the following claims.

What is claimed is:

1. An instrument seal of a surgical access device comprising:
   a plurality of nested coaxial seals arranged to cooperate and form a complete, circumferential seal around an inserted instrument, each of the plurality of nested coaxial seals forming a partial seal upon the inserted instrument and stretching in one direction in response to the inserted instrument;
   each of the plurality of nested coaxial seals has a cylindrical center portion and a distal tapered portion with an opening disposed in a portion of the distal tapered portion: and
   a seal housing defining an aperture extending through the seal housing and having a center aligned with a longitudinal axis, the opening of each of the plurality of nested coaxial seals having a center not aligned with the longitudinal axis.

2. The instrument seal of claim 1 wherein the openings of each of the plurality of nested coaxial seals cooperatively define an orifice with a center aligned with the longitudinal axis of the seal housing.

3. The instrument seal of claim 2 wherein the openings of each of the plurality of nested coaxial seals is larger than the orifice defined by the plurality of nested coaxial seals.

4. The instrument seal of claim 1 wherein at least one of the plurality of nested coaxial seals has a proximal flange.

5. The instrument seal of claim 1 wherein one of the plurality of nested coaxial seals has a proximal flange and the other plurality of nested coaxial seals is smooth without a proximal flange.

6. The instrument seal of claim 1 wherein at least one of the plurality of nested coaxial seals is impregnated with a material to facilitate withdrawal of the inserted instrument.

7. The instrument seal of claim 1 further comprising a raised portion attached to one of the plurality of nested coaxial seals to create a predetermined distance between at least two immediately adjacent seals of the plurality of nested coaxial seals.

8. The instrument seal of claim 1 wherein the opening of each of the plurality of nested coaxial seals is a triangular opening.

9. The instrument seal of claim 1 wherein the opening of each of the plurality of nested coaxial seals is an elliptical opening.

10. An instrument seal of a surgical access device comprising:
    a plurality of nested coaxial seals arranged to cooperate and form a complete, circumferential seal around an inserted instrument, each of the plurality of nested coaxial seals forming a partial seal upon the inserted instrument and stretching in one direction in response to the inserted instrument; and each of the plurality of nested coaxial seals has a cylindrical center portion and a distal tapered portion with an opening disposed in a portion of the distal tapered portion;

wherein the opening of each of the plurality of nested coaxial seals starts from a perimeter of the cylindrical center portion intersecting the distal tapered portion and extends towards and not past a center point of the distal tapered portion.

11. An instrument seal of a surgical access device comprising:

a plurality of nested coaxial seals arranged to cooperate and form a complete, circumferential seal around an inserted instrument, each of the plurality of nested coaxial seals forming a partial seal upon the inserted instrument and stretching in one direction in response to the inserted instrument; and each of the plurality of nested coaxial seals has a cylindrical center portion and a distal tapered portion with an opening disposed in a portion of the distal tapered portion;

wherein a center point of the distal tapered portion of each of the plurality of nested coaxial seals does not include an opening.

12. An instrument seal of a surgical access device comprising:

a plurality of nested coaxial seals arranged to cooperate and form a complete, circumferential seal around an inserted instrument, each of the plurality of nested coaxial seals forming a partial seal upon the inserted instrument and stretching in one direction in response to the inserted instrument; and each of the plurality of nested coaxial seals being elongate having a length greater than a width of the seal and each of the plurality of nested coaxial seals having a proximal opening and a distal opening, the proximal opening of each of the plurality of nested coaxial seals having a center aligned with a longitudinal axis of the instrument seal and the distal opening of each of the plurality of nested coaxial seals having a center not aligned with the longitudinal axis of the instrument seal, the length being a dimensional length along a portion of each of the plurality of nested coaxial seals that is longer and the width being a dimensional length along a radius of each of the plurality of nested coaxial seals that is shorter than the length;

wherein the plurality of nested coaxial seals comprises a first, second, third and fourth seal, the first seal nested within the second seal nested within the third seal nested within the fourth seal, the first and third seals being made of a puncture resistant material and the second and fourth seals being made of a compliant material and not puncture resistant.

13. The instrument seal of claim 12 wherein the plurality of nested coaxial seals are integrated into a monolithic structure.

14. The instrument seal of claim 12 wherein the distal opening of each of the plurality of nested coaxial seals occupies a quarter portion of a surface area of a distal most portion of each of the plurality of nested coaxial seals.

15. The instrument seal of claim 12 further comprising a zero seal and the plurality of nested coaxial seals nested within the zero seal.

16. The instrument seal of claim 15 wherein the zero seal is a duckbill made of a material being the same as the plurality of nested coaxial seals.

17. The instrument seal of claim 15 wherein the zero seal has a proximal flange.

18. The instrument seal of claim 15 wherein the zero seal forms a seal in the absence of the instrument inserted through the zero seal and the plurality of nested coaxial seals.

19. The instrument seal of claim 12 further comprising a seal housing with the plurality of nested coaxial seals disposed within the seal housing and a cannula removably coupled to the seal housing.

20. The instrument seal of claim 12 wherein the distal opening of each of the plurality of nested coaxial seals is non-circular.

21. The instrument seal of claim 12 wherein the fourth seal includes a raised portion attached to the fourth seal and disposed between the fourth seal and the third seal.

22. The instrument seal of claim 12 wherein the third seal includes a raised portion attached to the third seal and disposed between the third seal and the second seal.

23. The instrument seal of claim 22 wherein the second seal includes a raised portion attached to the second seal and disposed between the second seal and the first seal.

24. The instrument seal of claim 12 wherein at least one of the plurality of nested coaxial seals comprises a ramp along a portion of the distal opening of the at least one of the plurality of nested coaxial seals.

25. The instrument seal of claim 24 wherein at least one of the plurality of nested coaxial seals comprises raised portions attached to the at least one of the plurality of nested coaxial seals to create a predetermined distance between the at least one of the plurality of nested coaxial seals and another one of the at least one of the plurality of nested coaxial seals.

26. An instrument seal of a surgical access device comprising:

a plurality of nested coaxial seals arranged to cooperate and form a complete, circumferential seal around an inserted instrument, each of the plurality of nested coaxial seals forming a partial seal upon the inserted instrument and stretching in one direction in response to the inserted instrument; and each of the plurality of nested coaxial seals has a cylindrical center portion and a distal tapered portion with an opening disposed in a portion of the distal tapered portion;

wherein the opening of each of the plurality of nested coaxial seals is an elliptical opening;

wherein the opening of each of the plurality of nested coaxial seals is not suitable to seal against an entire outer diameter of an inserted instrument and each opening of each seal seals against only a portion of the inserted instrument.

* * * * *